(12) United States Patent
Aimi

(10) Patent No.: US 8,382,856 B2
(45) Date of Patent: Feb. 26, 2013

(54) HAIR DYE

(75) Inventor: Makiko Aimi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/517,916

(22) PCT Filed: Dec. 21, 2010

(86) PCT No.: PCT/JP2010/072983
§ 371 (c)(1),
(2), (4) Date: Jun. 20, 2012

(87) PCT Pub. No.: WO2011/078158
PCT Pub. Date: Jun. 30, 2011

(65) Prior Publication Data
US 2012/0255132 A1 Oct. 11, 2012

(30) Foreign Application Priority Data
Dec. 21, 2009 (JP) .................................. 2009-289289

(51) Int. Cl.
*A61Q 5/10* (2006.01)
*C07C 49/00* (2006.01)

(52) U.S. Cl. ............. 8/405; 8/595; 8/607; 8/616; 8/623; 568/332

(58) Field of Classification Search ............... 8/405, 595, 8/607, 616, 623; 568/332
See application file for complete search history.

(56) References Cited

U.S. PATENT DOCUMENTS 6,656,229 B1 12/2003 Taguchi et al.
2004/0055096 A1 3/2004 Taguchi et al.

FOREIGN PATENT DOCUMENTS

| JP | 04-013611 A | 1/1992 |
| JP | 04-164017 A | 6/1992 |
| JP | 06-072830 A | 3/1994 |
| JP | 2001-064134 A | 3/2001 |
| JP | 2002-138024 A | 5/2002 |
| JP | 2003-246716 A | 9/2003 |
| JP | 2004-035529 A | 2/2004 |
| JP | 2006-348011 A | 12/2006 |
| JP | 2008-273869 A | 11/2008 |
| JP | 2010-248103 A | 11/2010 |

OTHER PUBLICATIONS

English abstract of the Japanese Patent No. JP 2008273869 A dated Nov. 13, 2008.*
International Search Report of PCT/JP2010/072983 dated Apr. 19, 2011.

* cited by examiner

*Primary Examiner* — Eisa Elhilo
(74) *Attorney, Agent, or Firm* — Sughrue Mion, PLLC

(57) ABSTRACT

It is an object of the present invention to provide a safe hair dye, which requires a short hair dyeing time, has good hair dyeing property and color tone, and also has an effect of preventing photofading. The present invention provides a hair dye, which comprises a combination of (a) a first agent containing a substance reacting with iron to develop color and an ultraviolet absorbent having a 2-hydroxybenzophenone skeleton, and (b) a second agent containing iron salt.

20 Claims, No Drawings

HAIR DYE

CROSS REFERENCE TO RELATED APPLICATIONS

This application is a National Stage of International Application No. PCT/JP2010/072983 filed Dec. 21, 2010, claiming priority based on Japanese Patent Application No. 2009-289289 filed Dec. 21, 2009, the contents of all of which are incorporated herein by reference in their entirety.

TECHNICAL FIELD

The present invention relates to a non-oxidative hair dye having good light resistance, stainability, and safety.

BACKGROUND ART

Hair dye is generally classified into four types, namely, oxidative hair dye, ionic hair dye, temporary hair dye, and others. Among these hair dyes, an oxidative hair dye, which is most widely used at present, is also referred to as a permanent hair dye, and it is mainly constituted with paraphenylenediamine or para-aminophenol that becomes an active reaction intermediate as a result of oxidation by hydrogen peroxide. The active intermediate then reacts with a dye coupler molecule in hair, and it changes to a shampoo-resistant hair dye. However, the oxidative hair dye damages hair, may cause contact dermatitis or latent influence on total body for a long period of time, and may be suspected as mutagenicity or carcinogen. An ionic hair dye is also referred to as a semi-permanent hair dye, and it does not damage hair. However, the ionic hair dye is problematic in term of skin coloration upon dyeing, and the dye is washed off as a result of shampooing operation four to ten times. A temporary hair dye does not damage hair, and skin coloration is overcome by washing. However, the temporary hair dye is washed off as a result of a single shampooing operation.

As another hair dye, there has been proposed a non-oxidative hair dye which contains polyvalent phenol and iron salt (Patent Documents 1 to 3). However, previous non-oxidative hair dye products have required a long dyeing time, and their hair dyeing property and color tone have not been satisfactory.

By the way, a possible cause of the color fading of hair dye may be color fading due to light (ultraviolet light). The aforementioned patent documents describe that an ultraviolet absorbent can be added as necessary. However, there is a problem that, even if an ultraviolet absorbent is mixed into a hair dye for the purpose of protecting hair from ultraviolet light, a majority of the ultraviolet absorbent is rinsed off and its effects are hardly exhibited. Addition of a hydrophobic ultraviolet absorbent has also been proposed. However, the hydrophobic ultraviolet absorbent is problematic in that the direct use thereof causes poor solubility, and in that it is difficult to incorporate it into a composition (Patent Document 4).

PRIOR ART DOCUMENT

Patent Documents

[Patent Document 1] JP Patent Publication (Kokai) No. 4-164017 A (1992)
[Patent Document 2] JP Patent Publication (Kokai) No. 2003-246716 A
[Patent Document 3] JP Patent Publication (Kokai) No. 2008-273869 A
[Patent Document 4] JP Patent Publication (Kokai) No. 6-72830 A (1994)

SUMMARY OF INVENTION

Object to be Solved by the Invention

A conventional hair dye, which contains a plant extract or an organic compound that reacts with ion salt to develop color, has required a long hair dyeing time, and its hair dyeing property and color tone have not been satisfactory. In addition, the conventional hair dye has also been problematic in terms of color fading due to sunlight. It is an object of the present invention to provide a safe hair dye, which requires a short hair dyeing time, has good hair dyeing property and color tone, and also has an effect of preventing photofading.

Means for Solving the Object

As a result of intensive studies directed towards achieving the aforementioned object, the present inventors have found that the object can be achieved with a hair dye composition which contains one or more types of iron salts, one or more organic compounds or plant extracts reacting with the iron salts to develop color, and at least one type of ultraviolet absorbent reacting with the iron salts, thereby completing the present invention.

Thus, the present invention provides a hair dye, which comprises a combination of (a) a first agent containing a substance reacting with iron to develop color and an ultraviolet absorbent having a 2-hydroxybenzophenone skeleton, and (b) a second agent containing iron salt.

Preferably, the ultraviolet absorbent having a 2-hydroxybenzophenone skeleton is a compound having a ClogP value of 1 or more to 7 or less.

Preferably, the ultraviolet absorbent having a 2-hydroxybenzophenone skeleton is oxybenzone-1 or oxybenzone-3.

Preferably, the substance reacting with iron to develop color is at least one type selected from the group consisting of tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, *Scutellaria* root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, and luteolinidin.

Preferably, the substance reacting with iron to develop color is any one of the following (i) to (iii):
(i) a combination of tannic acid, gallic acid or a derivative thereof, salicylic acid or a derivative thereof, and *Scutellaria* root extract;
(ii) a combination of tannic acid, salicylic acid or a derivative thereof, and *Scutellaria* root extract; and
(iii) a combination of tannic acid and turmetic.

Preferably, the iron salt is ferrous sulfate, ferrous chloride, ferrous acetate, ferrous phosphate, ferrous oxalate, ferric sulfate, ferric chloride, or ferric acetate.

Preferably, the substance reacting with iron to develop color is used at 0.5% by weight to 10% by weight based on the total weight of the first agent, the ultraviolet absorbent having a 2-hydroxybenzophenone skeleton is used at 0.5% by weight to 10% by weight based on the total weight of the first agent, and the iron salt is used at 0.5% by weight to 10% by weight based on the total weight of the second agent.

The present invention further provides a method for dyeing hair, which comprises applying the aforementioned hair dye of the present invention to hair.

Effect of the Invention

The hair dye of the present invention requires a short hair dyeing time, has good hair dyeing property and color tone, and also has an effect of preventing photofading. In addition, the present hair dye is also excellent in terms of safety.

EMBODIMENTS FOR CARRYING OUT THE INVENTION

Hereinafter, the embodiments for carrying out the present invention will be described in detail.

The hair dye of the present invention is a two-agent hair dye which comprises a combination of (a) a first agent containing a substance reacting with iron to develop color and an ultraviolet absorbent having a 2-hydroxybenzophenone skeleton, and (b) a second agent containing iron salt.

As a substance reacting with iron to develop color used in the present invention, an organic compound or a plant extract that reacts with iron to develop color can be used. Specific examples of such a substance reacting with iron to develop color include, but are not limited to, tannic acid, gallic acid or a derivative thereof gallnut, pyrogallol, logwood, hematein, catechol, salicylic acid or a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, *Scutellaria* root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, and luteolinidin. Among the above examples, more preferred examples include tannic acid, gallic acid and a derivative thereof, salicylic acid and a derivative thereof, ferulic acid, turmeric extract, *Scutellaria* root extract, and quercetin. An example of the gallic acid derivative is an alkyl ester of gallic acid. An example of the gallic acid alkyl ester is a linear or branched alkyl ester containing 1 to 10, and preferably 2 to 5 carbon atoms. Specific examples of the gallic acid alkyl ester include ethyl gallate, propyl gallate, and isoamyl gallate. The gallic acid or a derivative thereof may be chemically synthesized according to a known method, or it may also be isolated from a plant. Moreover, it may also be prepared by further performing chemical synthesis on gallic acid or a derivative thereof isolated from a plant. Furthermore, an extract containing the gallic acid or a derivative thereof isolated from a plant may be directly used. For example, gallic acid derived from *Aralia elata* as a leguminous plant, gallic acid derived from gallnut produced from *Rhus javanica* as an anacardiaceous plant, or an extract containing the same may be used. Still further, a derivative obtained by chemically esterifying such gallic acid may also be used. Examples of the salicylic acid derivative include esters and salts of salicylic acid. Examples of the salicylic acid salt include alkali metal salts of salicylic acid. A specific example is sodium salicylate. An example of the salicylic acid ester is a linear or branched alkyl ester or phenyl ester containing 1 to 10 carbon atoms. Specific examples of the salicylic acid ester include octyl salicylate, phenyl salicylate, and methyl salicylate.

The amount of the substance reacting with iron to develop color used is not particularly limited, as long as the effects of the present invention are obtained. The substance is preferably used at 0.5% by weight to 10% by weight, and more preferably 1% by weight to 6% by weight, based on the total weight of the first agent.

As an ultraviolet absorbent having a 2-hydroxybenzophenone skeleton used in the present invention, a compound having a 2-hydroxybenzophenone skeleton, represented by the following formula (1), can be preferably used.

[Chem. 1]

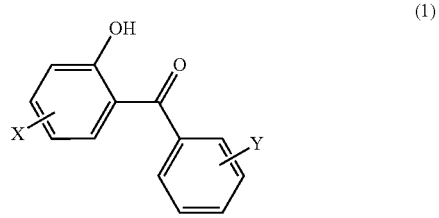

(1)

wherein X and Y independently represent a hydroxyl group, an alkoxy group containing 1 to 16 carbon atoms, an alkyl group containing 1 to 16 carbon atoms, a sulfo group, a carboxyl group, a halogen atom, or the like, wherein a plurality of substituents represented by X and Y may be present in each benzene ring.

Specific examples of the ultraviolet absorbent having a 2-hydroxybenzophenone skeleton used in the present invention include, but are not limited to, oxybenzone-1 (2,4-dihydroxybenzophenone), oxybenzone-3 (2-hydroxy-4-methoxybenzophenone), oxybenzone-4 (2-hydroxy-4-methoxybenzophenone sulfonate), oxybenzone-6 (2,2'-dihydroxy-4,4'-dimethoxybenzophenone), tetrahydroxybenzophenone, oxybenzone-9 (2,2'-dihydroxy-4,4'-dimethoxybenzophenone disulfonate), 4-ethoxy-2-hydroxybenzophenone, 4-(2-ethylhexyloxy)-2-hydroxybenzophenone, 5-amino-2-hydroxybenzophenone, 4-amino-2-hydroxybenzophenone, 4'-amino-2-hydroxybenzophenone, 2-hydroxy-5-chlorobenzophenone, 2-hydroxy-3,5-dichlorobenzophenone, 3',5-dichloro-2-hydroxy-benzophenone, 2-hydroxy-4'-methylbenzophenone, 2-hydroxy-4'-methoxybenzophenone, 2-hydroxy-5-methylbenzophenone, 2-hydroxy-4'-methylbenzophenone, and 2-hydroxy-3-tert-butylbenzophenone. Of these, more preferred examples include oxybenzone-1, oxybenzone-3, oxybenzone-4, oxybenzone-6, and tetrahydroxybenzophenone. Further preferred examples include oxybenzone-1 and oxybenzone-3.

As the ultraviolet absorbent having a 2-hydroxybenzophenone skeleton, a compound having a ClogP value of 1 or more to 7 or less can be preferably used. Using the compound having a ClogP value of 1 or more to 7 or less, a particularly favorable dyeing effect can be achieved. The reason therefor is assumed to be that, with the use of the compound having a ClogP value of 1 or more to 7 or less, the present compound also penetrates into hair, forms an iron chelate in the hair, and contributes to hair dyeing. It is to be noted that logP is a parameter indicating hydrophobicity and indicates an octanol-water partition coefficient. As a result of the development of the recent computational chemistry, it became possible to obtain a logP value by calculation based on computer. The thus obtained value is referred to as ClogP.

The structures of representative compounds of the ultraviolet absorbent having a 2-hydroxybenzophenone skeleton and the ClogP values thereof are shown below.

[Chem. 2]

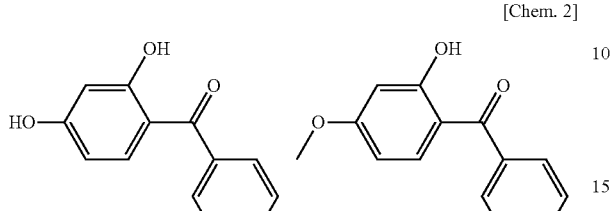

Chemical Formula: $C_{13}H_{10}O_3$
Exact Mass: 214.06
Log P: 2.46
tPSA: 57.53
Oxybenzone-1

Chemical Formula: $C_{14}H_{12}O_3$
Exact Mass: 228.08
Log P: 2.73
tPSA: 46.53
Oxybenzone-3

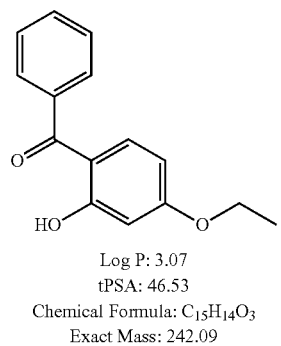

Log P: 3.07
tPSA: 46.53
Chemical Formula: $C_{15}H_{14}O_3$
Exact Mass: 242.09

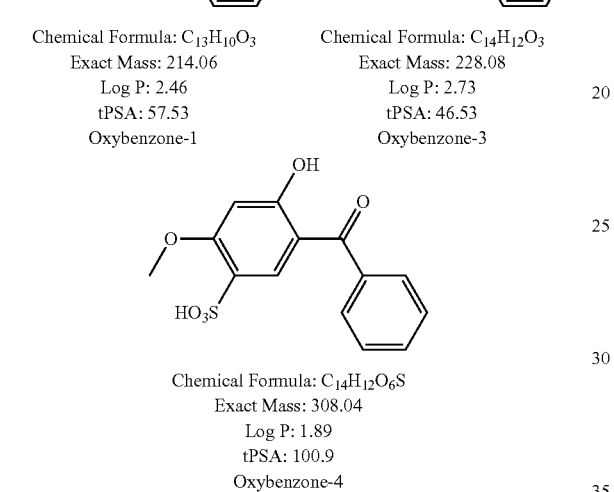

Chemical Formula: $C_{14}H_{12}O_6S$
Exact Mass: 308.04
Log P: 1.89
tPSA: 100.9
Oxybenzone-4

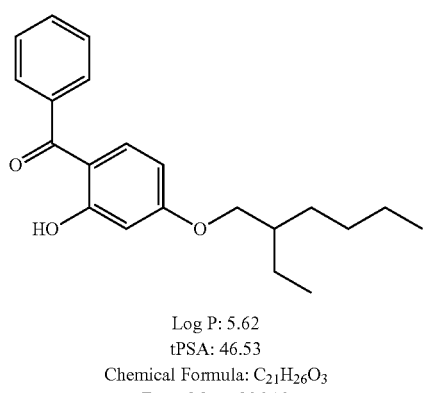

Log P: 5.62
tPSA: 46.53
Chemical Formula: $C_{21}H_{26}O_3$
Exact Mass: 326.19

[Chem. 3]

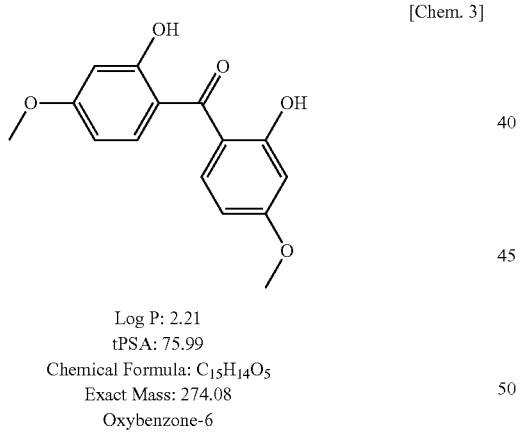

Log P: 2.21
tPSA: 75.99
Chemical Formula: $C_{15}H_{14}O_5$
Exact Mass: 274.08
Oxybenzone-6

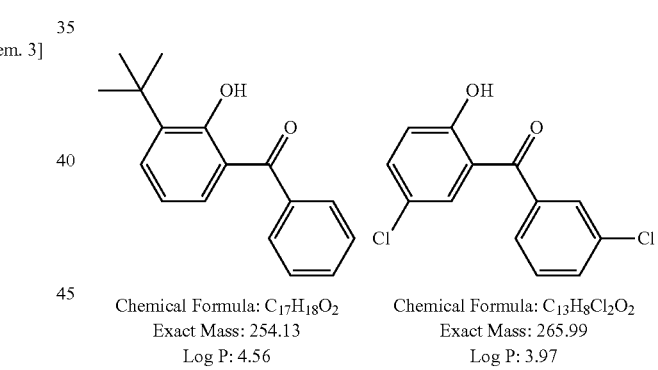

Chemical Formula: $C_{17}H_{18}O_2$
Exact Mass: 254.13
Log P: 4.56
tPSA: 37.3

Chemical Formula: $C_{13}H_8Cl_2O_2$
Exact Mass: 265.99
Log P: 3.97
tPSA: 37.3

[Chem. 4]

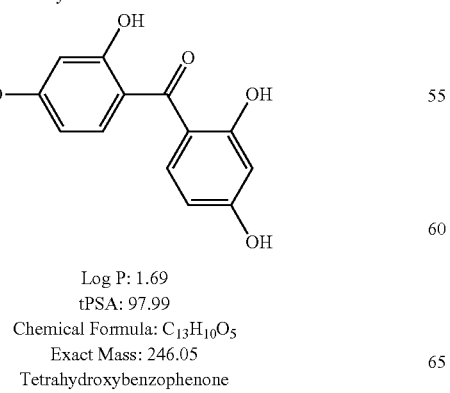

Log P: 1.69
tPSA: 97.99
Chemical Formula: $C_{13}H_{10}O_5$
Exact Mass: 246.05
Tetrahydroxybenzophenone

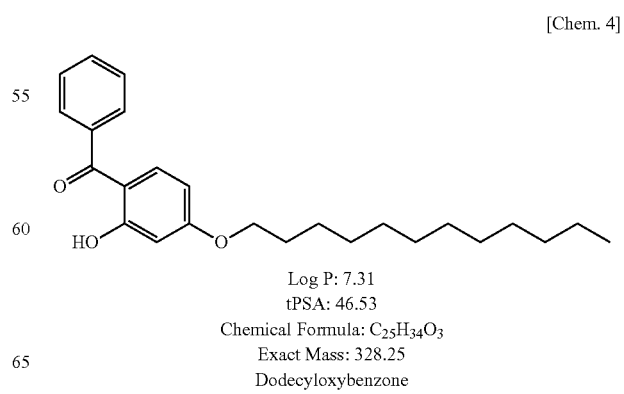

Log P: 7.31
tPSA: 46.53
Chemical Formula: $C_{25}H_{34}O_3$
Exact Mass: 328.25
Dodecyloxybenzone

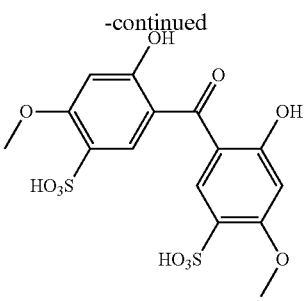

Log P: 0.53
tPSA: 184.73
Chemical Formula: $C_{15}H_{14}O_{11}S_2$
Exact Mass: 434.00
Oxybenzone-9

The amount of the ultraviolet absorbent having a 2-hydroxybenzophenone skeleton used is not particularly limited, as long as the effects of the present invention can be obtained. The ultraviolet absorbent having a 2-hydroxybenzophenone skeleton is preferably used at 0.5% by weight to 10% by weight, and more preferably I % by weight to 6% by weight, based on the total weight of the first agent.

The type of the iron salt used in the present invention is not particularly limited, as long as the effects of the present invention can be obtained. In general, ferrous sulfate, ferrous chloride, ferrous acetate, ferrous phosphate, ferrous oxalate, ferric sulfate, ferric chloride, ferric acetate, or the like can be used. Of these, ferrous sulfate or ferric chloride is preferable.

The amount of the iron salt used is not particularly limited, as long as the effects of the present invention can be obtained. The iron salt is preferably used at 0.5% by weight to 10% by weight, and more preferably 1% by weight to 6% by weight, based on the total weight of the second agent.

The first agent and/or second agent that constitute(s) the hair dye of the present invention may also comprise various types of additives, in addition to the aforementioned compounds. Examples of the additives include a base, a surfactant, oils and fats, a solvent, a thickener, organic acid, an antiseptic, an antioxidant, a pH adjuster, a wetting agent, perfume, a metallic taste masking agent, a coloring agent for products, and an ultraviolet absorbent for products. As such additives, ingredients used for ordinary cosmetic products, such as a hair restorer/hair growth stimulant, an anti-dandruff agent, an antibacterial agent, a softener, a moisturizer, an active oxygen removing agent, an antioxidant, an antimicrobial agent, silicone, mineral, a protein hydrolysate, a peptide, and amino acids, may be mixed, as appropriate, within a range that does not impair the object of the present invention. The amounts of these additives used may be determined, as appropriate, within a range in which the effects of the present invention are exhibited.

Examples of the base include higher alcohols, hydrocarbon, fatty acid ester, vegetable oil, and fatty acid. Examples of the surfactant include polyoxyethylene alkyl ether, polyoxyethylene polyoxypropylene alkyl ether, glycerin fatty acid ester, polyglycerin fatty acid ester, polyethylene glycol fatty acid ester, polyoxyethylene alkyl ether phosphate and a salt thereof, alkylglucoside, N-acylamino acid salt, alkyl ether carboxylate, alkyl sulfate, polyoxyethylene alkyl ether sulfate, sulfonate, alkyl ammonium salt, and alkyl amide propyl betaine. Examples of the antioxidant include ascorbic acid and a derivative thereof, and sodium sulfite. Examples of the pH adjuster include citric acid, phosphoric acid, ammonia, ammonium bicarbonate, ammonium carbonate, potassium hydroxide, sodium hydroxide, monoethanolamine, isopropanolamine, ammonium phosphate, diammonium monohydrogen phosphate, sodium citrate, ammonium citrate, potassium phosphate, and sodium phosphate. Examples of the wetting agent include 1,3-butylene glycol, propylene glycol, glycerin, sorbitol, sodium pyrroridonecarboxylate, amino acid, and vegetable oil. Examples of the thickener include xanthan gum, polyethylene glycol, and hydroxyethyl cellulose. Examples of the solvent include water, ethanol, isopropyl alcohol, 1,3-butylene glycol, 1,2-pentanediol, 2-methyl-2,4-pentanediol, glycerin, diglycerin, propylene glycol, and dipropylene glycol.

The hair dye of the present invention is a two-agent hair dye that is composed of a first agent and a second agent, and hair dyeing is carried out by mixing the first agent with the second agent. The first agent comprises a substance reacting with iron to develop color and an ultraviolet absorbent having a 2-hydroxybenzophenone skeleton, whereas the second agent comprises iron salt.

The ratio between the first agent and the second agent is the first agent:the second agent=about 1:0.5 to 1:2 at a weight ratio, and particularly preferably, the first agent:the second agent=about 1:1 at a weight ratio.

The pH of the first agent is preferably pH 6 to 10, and more preferably pH 7 to 9. The pH of the second agent is preferably pH 2 to 6, and more preferably pH 3 to 5.

Examples of the dosage form of the hair dye of the present invention include cream, liquid gel, emulsion, spray, and aerosol. Of these, aerosol is preferable. The aerosol can be produced by filling a pressure-resistant container with the hair dye (the first agent or the second agent), compressed gas, a surfactant, a thickener, liquefied gas, etc. under an anaerobic atmosphere. The compressed gas used herein is preferably nitrogen gas, carbonic acid gas, argon gas, or the like.

Hair dyeing can be carried out by applying the above-described hair dye of the present invention to hair. As a method for applying the hair dye of the present invention to hair, the first agent may be first applied to the hair and may be then left for a predetermined period of time. Then, the second agent may be applied to the hair and may be then left for a predetermined period of time. Thereafter, the agents may be washed off. Alternatively, the first agent and the second agent may be simultaneously applied to hair, and may be then left for a predetermined period of time, followed by washing them off.

With regard to the amount of the hair dye of the present invention applied, it is preferable to apply approximately 30 to 70 g of the first agent and approximately 30 to 70 g of the second agent to hair having a length of approximately 20 can. It is more preferable to apply approximately 40 to 60 g of the first agent and approximately 40 to 60 g of the second agent to the aforementioned hair. As an example, 50 g of the first agent and 50 g of the second agent may be applied.

Hereinafter, the present invention will be more specifically described in the following examples. However, these examples are not intended to limit the scope of the present invention.

EXAMPLES

Hair Dyeing Effects:

Hair dye compositions having the compositions shown in Tables 1 to 4 were produced by an ordinary method. The numerical value of each compound shown in the tables indicates % by weight based on the total weights of the first agent and the second agent. These compositions were evaluated in terms of hair dyeing property by the following method. The results are shown in Tables 1 to 4. The amounts of sodium hydroxide and hydrochloric acid are amounts necessary for adjusting the pH to the values shown in the tables.

Hair Dyeing Method:

2 g of the first agent was applied to 1 g of a white human hair bundle (100% white; part number: BM-W; manufactured by Beaulax) having a length of approximately 10 cm, and it was then spread thereon uniformly. Then, it was left for the indicated period of time. Thereafter, 2 g of the second agent was applied thereto and was then spread thereon uniformly, followed by leaving it for the indicated period of time. Thereafter, the hair bundle was subjected to shampooing and rinsing treatments, and it was then dried with a dryer.

Method for Evaluating Hair Dyeing Property:

The color of each hair bundle was measured with Chroma Meter CR200 manufactured by Minolta Corp. Hair dyeing property was evaluated based on the color difference (ΔE value) from the original white hair in accordance with the following standards.

A: ΔE value >30 (White hair is found fully colored by visual observation.)
B: 20<ΔE value <30 (White hair is found colored by visual observation)
C: 10<ΔE value <20 (White hair is found slightly colored by visual observation)
D: ΔE value <10 (White hair is found hardly colored by visual observation)

Method for Evaluating Color Tone:

The color tone of each hair bundle was evaluated by visual observation. When the hair bundle had any one of six preferred color tones, it was evaluated in accordance with the following standards. When the color tone of the hair bundle was not preferable, it was evaluated as "Bad". The color tone evaluated by visual observation was described in individual parentheses.

Good BK: Black
Good B: Brown
Good LB: Light brown
Good DB: Dark brown
Good RB: Reddish brown
Good AB: Ash brown Method for Evaluating the Effect of Preventing Photofading:

A hair bundle, which had been exposed to sunlight, was evaluated in accordance with the following standards:

Good: Almost the same color as that before exposure to sunlight
Bad: Color faded rather than that before exposure to sunlight

TABLE 1

| | | Example 1 | Example 2 | Example 3 | Example 4 | Example 5 | Example 6 |
|---|---|---|---|---|---|---|---|
| First agent | Tannic acid | 3.0 | 0.2 | | | | |
| | Gallic acid | | | 2.0 | | | |
| | Propyl gallate | | | | 0.5 | | |
| | Pyrogallol | | | | | 2.0 | |
| | Hematein | | | | | | 3.0 |
| | Tea extract | | | | | | |
| | Cochineal | | | | | | |
| | Hinokitiol | | | | | | |
| | Sodium salicylate | | | | | | |
| | Kaoliang | | | | | | |
| | Turmeric | | | | | | |
| | Oxybenzone-1 | | | | 2.0 | | 2.0 |
| | Oxybenzone-3 | 2.0 | 2.0 | | | 2.0 | |
| | Oxybenzone-4 | | | | | | |
| | Oxybenzone-6 | | | | 2.0 | | |
| | Tetrahydroxybenzophenone | | | | | | |
| | Ethanol | 5 | 5 | 5 | 5 | 5 | 5 |
| | Benzyl alcohol | 10 | 10 | 10 | 10 | 10 | 10 |
| | Sodium hydroxide | q.s. | q.s. | q.s. | q.s. | q.s. | q.s. |
| | Purified water | Balance | Balance | Balance | Balance | Balance | Balance |
| | pH | 8 | 8 | 8 | 8 | 8 | 8 |
| | Leaving time | 5 | 5 | 5 | 5 | 5 | 5 |
| Second agent | Ferrous sulfate | 2.0 | 2.0 | 1.0 | 2.0 | | 2.0 |
| | Ferric chloride | | | | | 2.0 | |
| | Sodium hydroxide | q.s. | q.s. | q.s. | q.s. | q.s. | q.s. |
| | Hydrochloric acid | q.s. | q.s. | q.s. | q.s. | q.s. | q.s. |
| | Purified water | Balance | Balance | Balance | Balance | Balance | Balance |
| | pH | 4 | 4 | 4 | 4 | 4 | 4 |
| | Leaving time | 10 | 10 | 10 | 10 | 10 | 10 |
| Hair dyeing results | | A | A | A | A | A | A |
| Color tone | | Good BK | Good B | Good BK | Good BK | Good BK | Good BK |
| Photofading preventive effect | | Good | Good | Good | Good | Good | Good |

| | | Example 7 | Example 8 | Example 9 | Example 10 | Example 11 | Example 12 |
|---|---|---|---|---|---|---|---|
| First agent | Tannic acid | | | | | | |
| | Gallic acid | | | | | | |
| | Propyl gallate | | | | | | |
| | Pyrogallol | | | | | | |
| | Hematein | | | | | | |
| | Tea extract | 3.0 | | | | | |
| | Cochineal | | 3.0 | | | | |
| | Hinokitiol | | | 0.5 | | | |
| | Sodium salicylate | | | | 3.0 | | |
| | Kaoliang | | | | | 3.0 | |
| | Turmeric | | | | | | 2.0 |

TABLE 1-continued

|  |  |  |  |  |  |  |
|---|---|---|---|---|---|---|
| Oxybenzone-1 |  |  |  |  |  |  |
| Oxybenzone-3 |  |  | 2.0 | 2.0 | 2.0 | 2.0 |
| Oxybenzone-4 |  | 2.0 |  |  |  |  |
| Oxybenzone-6 |  |  |  |  |  |  |
| Tetrahydroxybenzophenone | 2.0 |  |  |  |  |  |
| Ethanol | 5 | 5 | 5 | 5 | 5 | 5 |
| Benzyl alcohol | 10 | 10 | 10 | 10 | 10 | 10 |
| Sodium hydroxide | q.s. | q.s. | q.s. | q.s. | q.s. | q.s. |
| Purified water | Balance | Balance | Balance | Balance | Balance | Balance |
| pH | 8 | 8 | 8 | 8 | 8 | 8 |
| Leaving time | 5 | 5 | 5 | 5 | 5 | 5 |
| Second agent Ferrous sulfate | 2.0 | 1.0 |  | 2.0 | 2.0 | 2.0 |
| Ferric chloride |  |  | 2.0 |  |  |  |
| Sodium hydroxide | q.s. | q.s. | q.s. | q.s. | q.s. | q.s. |
| Hydrochloric acid | q.s. | q.s. | q.s. | q.s. | q.s. | q.s. |
| Purified water | Balance | Balance | Balance | Balance | Balance | Balance |
| pH | 4 | 4 | 4 | 4 | 4 | 4 |
| Leaving time | 10 | 10 | 10 | 10 | 10 | 10 |
| Hair dyeing results | B | A | A | B | A | B |
| Color tone | Good BK | Good BK | Good RB | Good RB | Good RB | Good DB |
| Photofading preventive effect | Good | Good | Good | Good | Good | Good |

TABLE 2

|  |  | Example 13 | Example 14 | Example 15 | Example 16 | Example 17 | Example 18 |
|---|---|---|---|---|---|---|---|
| First agent | Tannic acid |  |  |  | 1.0 | 0.2 | 0.2 |
|  | Propyl gallate |  |  |  | 0.2 |  |  |
|  | Sodium salicylate |  |  |  | 1.0 |  |  |
|  | Kaoliang |  |  |  |  |  | 2.0 |
|  | Scutellaria root extract |  |  |  | 0.5 |  | 0.5 |
|  | Quercetin | 3.0 |  |  |  |  |  |
|  | Turmeric |  | 2.0 |  |  | 2.0 |  |
|  | Ferulic acid |  |  | 2.0 |  |  |  |
|  | Oxybenzone-3 | 2.0 | 2.0 | 2.0 | 2.0 | 2.0 | 2.0 |
|  | Ethanol | 5 | 5 | 5 | 5 | 5 | 5 |
|  | Benzyl alcohol | 10 | 10 | 10 | 10 | 10 | 10 |
|  | Sodium hydroxide | q.s. | q.s. | q.s. | q.s. | q.s. | q.s. |
|  | Purified water | Balance | Balance | Balance | Balance | Balance | Balance |
|  | pH | 8 | 8 | 8 | 8 | 8 | 8 |
|  | Leaving time | 5 | 5 | 5 | 5 | 5 | 5 |
| Second agent | Ferrous sulfate | 2.0 | 2.0 | 2.0 | 2.0 | 2.0 | 2.0 |
|  | Sodium hydroxide | q.s. | q.s. | q.s. | q.s. | q.s. | q.s. |
|  | Hydrochloric acid | q.s. | q.s. | q.s. | q.s. | q.s. | q.s. |
|  | Purified water | Balance | Balance | Balance | Balance | Balance | Balance |
|  | pH | 4 | 4 | 4 | 4 | 4 | 4 |
|  | Leaving time | 10 | 10 | 10 | 10 | 10 | 10 |
| Hair dyeing results |  | A | A | A | A | A | A |
| Color tone |  | Good DB | Good LB | Good LB | Good BK | Good LB | Good DB |
| Photofading preventive effect |  | Good | Good | Good | Good | Good | Good |

|  |  | Example 19 | Example 20 | Example 21 | Example 22 | Example 23 | Example 24 |
|---|---|---|---|---|---|---|---|
| First agent | Tannic acid | 0.2 | 0.2 | 0.2 | 0.2 | 0.2 | 0.2 |
|  | Propyl gallate |  |  |  |  |  |  |
|  | Sodium salicylate | 1.0 | 1.0 | 1.0 | 1.0 | 1.0 | 1.0 |
|  | Kaoliang |  |  |  |  |  |  |
|  | Scutellaria root extract |  | 0.5 | 0.5 | 0.5 | 0.5 | 0.5 |
|  | Quercetin | 0.5 |  |  |  |  |  |
|  | Turmeric |  |  |  |  |  |  |
|  | Ferulic acid |  |  |  |  |  |  |
|  | Oxybenzone-3 | 2.0 | 2.0 | 2.0 | 2.0 | 2.0 | 2.0 |
|  | Ethanol | 5 | 5 | 5 | 5 | 5 | 5 |
|  | Benzyl alcohol | 10 | 10 | 10 | 10 | 10 | 10 |
|  | Sodium hydroxide | q.s. | q.s. | q.s. | q.s. | q.s. | q.s. |
|  | Purified water | Balance | Balance | Balance | Balance | Balance | Balance |
|  | pH | 8 | 8 | 8 | 9 | 8 | 8 |
|  | Leaving time | 5 | 5 | 5 | 5 | 5 | 0 |
| Second agent | Ferrous sulfate | 2.0 | 2.0 | 2.0 | 2.0 | 2.0 | 2.0 |
|  | Sodium hydroxide | q.s. | q.s. | q.s. | q.s. | q.s. | q.s. |
|  | Hydrochloric acid | q.s. | q.s. | q.s. | q.s. | q.s. | q.s. |

TABLE 2-continued

|  |  |  |  |  |  |  |
|---|---|---|---|---|---|---|
| Purified water | Balance | Balance | Balance | Balance | Balance | Balance |
| pH | 4 | 4 | 5 | 4 | 4 | 4 |
| Leaving time | 10 | 10 | 10 | 10 | 2 | 10 |
| Hair dyeing results | A | A | A | A | A | B |
| Color tone | Good DB | Good DB | Good DB | Good DB | Good DB | Good DB |
| Photofading preventive effect | Good | Good | Good | Good | Good | Good |

TABLE 3

|  |  | Compative Example 1 | Compative Example 2 | Compative Example 3 | Compative Example 4 | Comparative Example 5 | Comparative Example 6 | Comparaive Example 7 |
|---|---|---|---|---|---|---|---|---|
| First agent | Tannic acid | 3.0 |  |  |  |  | 0.2 | 0.2 |
|  | Pyrogallol |  | 2.0 |  |  |  |  |  |
|  | Sodium salicylate |  |  | 2.0 |  |  | 1.0 | 1.0 |
|  | Scutellaria root extract |  |  |  |  |  | 0.5 | 0.5 |
|  | Quercetin |  |  |  | 3.0 |  |  |  |
|  | Turmeric |  |  |  |  | 2.0 |  |  |
|  | Ethanol | 5 | 5 | 5 | 5 | 5 | 5 | 5 |
|  | Benzyl alcohol | 10 | 10 | 10 | 10 | 10 | 10 | 10 |
|  | Sodium hydroxide | q.s. | q.s. | q.s. | q.s. | q.s. | q.s. | q.s. |
|  | Purified water | Balance | Balance | Balance | Balance | Balance | Balance | Balance |
|  | pH | 8 | 8 | 8 | 8 | 8 | 8 | 8 |
|  | Leaving time | 5 | 5 | 5 | 5 | 5 | 5 | 5 |
| Second agent | Ferrous sulfate | 2.0 | 2.0 | 2.0 | 2.0 | 2.0 | 2.0 | 2.0 |
|  | Sodium hydroxide | q.s. | q.s. | q.s. | q.s. | q.s. | q.s. | q.s. |
|  | Hydrochloric acid | q.s. | q.s. | q.s. | q.s. | q.s. | q.s. | q.s. |
|  | Purified water | Balance | Balance | Balance | Balance | Balance | Balance | Balance |
|  | pH | 4 | 4 | 4 | 4 | 4 | 4 | 4 |
|  | Leaving time | 10 | 10 | 10 | 10 | 10 | 10 | 2 |
| Hair dyeing results |  | B | C | C | C | C | C | D |
| Color tone |  | Bad Purple | Good BK | Bad AB | Bad Green | Bad Yellow | Good AB | Good AB |
| Photofading preventive effect |  | Bad | Bad | Bad | Bad | Bad | Bad | Bad |

TABLE 4

|  |  | Example 25 | Example 26 | Comparative Example 8 | Comparative Example 9 | Comparative Example 10 |
|---|---|---|---|---|---|---|
| First agent | Tannic acid | 0.2 | 0.2 | 0.2 | 0.2 | 0.2 |
|  | Sodium salicylate | 1.0 | 1.0 | 1.0 | 1.0 | 1.0 |
|  | Scutellaria root extract | 0.5 | 0.5 | 0.5 | 0.5 | 0.5 |
|  | Oxybenzone-9 | 2.0 |  |  |  |  |
|  | Dodecyloxybenzone |  | 2.0 |  |  |  |
|  | Sodium 4-methoxycinnamate |  |  | 2.0 |  |  |
|  | Ethylhexyl methoxycinnamate |  |  |  | 2.0 |  |
|  | Ethylhexyl salicylate |  |  |  |  | 2.0 |
|  | Methylenebisbenzotriazolyltetramethylbutylphenol |  |  |  |  |  |
|  | Bumetrizole |  |  |  |  |  |
|  | Octocrylene |  |  |  |  |  |
|  | Homosalate |  |  |  |  |  |
|  | Ethanol | 5 | 5 | 5 | 5 | 5 |
|  | Benzyl alcohol | 10 | 10 | 10 | 10 | 10 |
|  | Sodium hydroxide | q.s. | q.s. | q.s. | q.s. | q.s. |
|  | Purified water | Balance | Balance | Balance | Balance | Balance |
|  | pH | 8 | 8 | 8 | 8 | 8 |
|  | Leaving time | 5 | 5 | 5 | 5 | 5 |
| Second agent | Ferrous sulfate | 2.0 | 2.0 | 2.0 | 2.0 | 2.0 |
|  | Sodium hydroxide | q.s. | q.s. | q.s. | q.s. | q.s. |
|  | Hydrochloric acid | q.s. | q.s. | q.s. | q.s. | q.s. |
|  | Purified water | Balance | Balance | Balance | Balance | Balance |
|  | pH | 4 | 4 | 4 | 4 | 4 |
|  | Leaving time | 10 | 10 | 10 | 10 | 10 |
| Hair dyeing results |  | C | C | C | C | C |
| Color tone |  | Good AB | Good AB | Good AB | Good AB | Good AB |
| Photofading preventive effect |  | Good | Good | Bad | Bad | Bad |

|  |  | Comparative Example 11 | Comparative Example 12 | Comparative Example 13 | Comparative Example 14 |
|---|---|---|---|---|---|
| First agent | Tannic acid | 0.2 | 0.2 | 0.2 | 0.2 |
|  | Sodium salicylate | 1.0 | 1.0 | 1.0 | 1.0 |
|  | Scutellaria root extract | 0.5 | 0.5 | 0.5 | 0.5 |
|  | Oxybenzone-9 |  |  |  |  |
|  | Dodecyloxybenzone |  |  |  |  |

TABLE 4-continued

| | | | | | |
|---|---|---|---|---|---|
| | Sodium 4-methoxycinnamate | | | | |
| | Ethylhexyl methoxycinnamate | | | | |
| | Ethylhexyl salicylate | | | | |
| | Methylenebisbenzotriazolyltetramethylbutylphenol | 2.0 | | | |
| | Bumetrizole | | 2.0 | | |
| | Octocrylene | | | 2.0 | |
| | Homosalate | | | | 2.0 |
| | Ethanol | 5 | 5 | 5 | 5 |
| | Benzyl alcohol | 10 | 10 | 10 | 10 |
| | Sodium hydroxide | q.s. | q.s. | q.s. | q.s. |
| | Purified water | Balance | Balance | Balance | Balance |
| | pH | 8 | 8 | 8 | 8 |
| | Leaving time | 5 | 5 | 5 | 5 |
| Second agent | Ferrous sulfate | 2.0 | 2.0 | 2.0 | 2.0 |
| | Sodium hydroxide | q.s. | q.s. | q.s. | q.s. |
| | Hydrochloric acid | q.s. | q.s. | q.s. | q.s. |
| | Purified water | Balance | Balance | Balance | Balance |
| | pH | 4 | 4 | 4 | 4 |
| | Leaving time | 10 | 10 | 10 | 10 |
| Hair dyeing results | | C | C | C | C |
| Color tone | | Good AB | Good AB | Good AB | Good AB |
| Photofading preventive effect | | Bad | Bad | Bad | Bad |

*q.s.: quantum sufficiat (= appropriate amount)

The invention claimed is:

1. A hair dye, which comprises a combination of (a) a first agent containing a substance reacting with iron to develop color and an ultraviolet absorbent having a 2-hydroxybenzophenone skeleton, and (b) a second agent containing iron salt.

2. The hair dye according to claim 1, wherein the ultraviolet absorbent having a 2-hydroxybenzophenone skeleton is a compound having a ClogP value of 1 or more to 7 or less.

3. The hair dye according to claim 1, wherein the ultraviolet absorbent having a 2-hydroxybenzophenone skeleton is oxybenzone-1 or oxybenzone-3.

4. The hair dye according to claim 1, wherein the substance reacting with iron to develop color is at least one type selected from the group consisting of tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, *Scutellaria* root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, and luteolinidin.

5. The hair dye according to claim 2, wherein the substance reacting with iron to develop color is at least one type selected from the group consisting of tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, *Scutellaria* root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, and luteolinidin.

6. The hair dye according to claim 3, wherein the substance reacting with iron to develop color is at least one type selected from the group consisting of tannic acid, gallic acid and a derivative thereof, gallnut, pyrogallol, logwood, hematein, catechol, salicylic acid and a derivative thereof, phthalic acid, eugenol, isoeugenol, nicotinic-acid amide, dehydroacetic acid, pyridoxine, ellagic acid, kojic acid, maltol, ferulic acid, hinokitiol, turmeric extract, curcumin, *Scutellaria* root extract, onion extract, quercetin, rutin, hesperetin, hesperidin, fresh coffee bean extract, caffeic acid, chlorogenic acid, tea extract, catechin, epicatechin, lithospermi radix extract, Japanese basil extract, shisonin, grape leaf extract, grape extract, enocyanin, laccaic acid, lac, cochineal, carminic acid, elderberry, red cabbage, purple sweet potato, tamarind, kaoliang, apigeninidin, and luteolinidin.

7. The hair dye according to claim 1, wherein the substance reacting with iron to develop color is any one of the following (i) to (iii):
   (i) a combination of tannic acid, gallic acid or a derivative thereof, salicylic acid or a derivative thereof, and *Scutellaria* root extract;
   (ii) a combination of tannic acid, salicylic acid or a derivative thereof, and *Scutellaria* root extract; and
   (iii) a combination of tannic acid and turmetic.

8. The hair dye according to claim 2, wherein the substance reacting with iron to develop color is any one of the following (i) to (iii):
   (i) a combination of tannic acid, gallic acid or a derivative thereof, salicylic acid or a derivative thereof, and *Scutellaria* root extract;
   (ii) a combination of tannic acid, salicylic acid or a derivative thereof, and *Scutellaria* root extract; and
   (iii) a combination of tannic acid and turmetic.

9. The hair dye according to claim 3, wherein the substance reacting with iron to develop color is any one of the following (i) to (iii):
   (i) a combination of tannic acid, gallic acid or a derivative thereof, salicylic acid or a derivative thereof, and *Scutellaria* root extract;
   (ii) a combination of tannic acid, salicylic acid or a derivative thereof, and *Scutellaria* root extract; and
   (iii) a combination of tannic acid and turmetic.

10. The hair dye according to claim 1, wherein the iron salt is ferrous sulfate, ferrous chloride, ferrous acetate, ferrous phosphate, ferrous oxalate, ferric sulfate, ferric chloride, or ferric acetate.

11. The hair dye according to claim 2, wherein the iron salt is ferrous sulfate, ferrous chloride, ferrous acetate, ferrous phosphate, ferrous oxalate, ferric sulfate, ferric chloride, or ferric acetate.

12. The hair dye according to claim 3, wherein the iron salt is ferrous sulfate, ferrous chloride, ferrous acetate, ferrous phosphate, ferrous oxalate, ferric sulfate, ferric chloride, or ferric acetate.

13. The hair dye according to claim 4, wherein the iron salt is ferrous sulfate, ferrous chloride, ferrous acetate, ferrous phosphate, ferrous oxalate, ferric sulfate, ferric chloride, or ferric acetate.

14. The hair dye according to claim 5, wherein the iron salt is ferrous sulfate, ferrous chloride, ferrous acetate, ferrous phosphate, ferrous oxalate, ferric sulfate, ferric chloride, or ferric acetate.

15. The hair dye according to claim 1, wherein the substance reacting with iron to develop color is used at 0.5% by weight to 10% by weight based on the total weight of the first agent, the ultraviolet absorbent having a 2-hydroxybenzophenone skeleton is used at 0.5% by weight to 10% by weight based on the total weight of the first agent, and the iron salt is used at 0.5% by weight to 10% by weight based on the total weight of the second agent.

16. The hair dye according to claim 3, wherein the substance reacting with iron to develop color is used at 0.5% by weight to 10% by weight based on the total weight of the first agent, the ultraviolet absorbent having a 2-hydroxybenzophenone skeleton is used at 0.5% by weight to 10% by weight based on the total weight of the first agent, and the iron salt is used at 0.5% by weight to 10% by weight based on the total weight of the second agent.

17. The hair dye according to claim 4, wherein the substance reacting with iron to develop color is used at 0.5% by weight to 10% by weight based on the total weight of the first agent, the ultraviolet absorbent having a 2-hydroxybenzophenone skeleton is used at 0.5% by weight to 10% by weight based on the total weight of the first agent, and the iron salt is used at 0.5% by weight to 10% by weight based on the total weight of the second agent.

18. The hair dye according to claim 5, wherein the substance reacting with iron to develop color is used at 0.5% by weight to 10% by weight based on the total weight of the first agent, the ultraviolet absorbent having a 2-hydroxybenzophenone skeleton is used at 0.5% by weight to 10% by weight based on the total weight of the first agent, and the iron salt is used at 0.5% by weight to 10% by weight based on the total weight of the second agent.

19. The hair dye according to claim 10, wherein the substance reacting with iron to develop color is used at 0.5% by weight to 10% by weight based on the total weight of the first agent, the ultraviolet absorbent having a 2-hydroxybenzophenone skeleton is used at 0.5% by weight to 10% by weight based on the total weight of the first agent, and the iron salt is used at 0.5% by weight to 10% by weight based on the total weight of the second agent.

20. A method for dyeing hair, which comprises applying the hair dye according to claim 1 to hair.

* * * * *